United States Patent [19]

Sheppard et al.

[11] 3,956,366

[45] May 11, 1976

[54] N-MONOHALOMONOSUBSTITUTED UREAS

[75] Inventors: Chester Stephen Sheppard, Tonawanda; Leonard Earnest Korczykowski, North Tonawanda, both of N.Y.

[73] Assignee: Pennwalt Corporation, Philadelphia, Pa.

[22] Filed: June 28, 1973

[21] Appl. No.: 374,445

Related U.S. Application Data

[60] Division of Ser. No. 684,651, Nov. 21, 1967, Pat. No. 3,746,760, which is a continuation-in-part of Ser. No. 409,306, Nov. 5, 1964, abandoned.

[52] U.S. Cl. ......................... 260/482 C; 260/479 C
[51] Int. Cl.$^2$ ....................................... C07C 125/06
[58] Field of Search ..................... 260/482 C, 479 C

[56] References Cited
UNITED STATES PATENTS

| | | | |
|---|---|---|---|
| 3,706,788 | 12/1972 | Grakauskas | 260/482 C |
| 3,729,504 | 4/1973 | Grakauskas | 260/482 C |
| 3,851,013 | 11/1974 | Perrey | 260/482 C |

*Primary Examiner*—Lorraine A. Weinberger
*Assistant Examiner*—P. J. Killos
*Attorney, Agent, or Firm*—Charles E. Feeny

[57] ABSTRACT

A process for making N-monochloro or bromo monosubstituted urea where a urea $RNH-CO-NH_2$ is suspended in liquid water at 0°C–60°C and reacted with free chlorine or free bromine, at least 2 g. atoms per mole of urea, preferably in the presence of an acid acceptor such as zinc oxide; R may be alkyl having 3 carbon atoms, cycloalkyl, aralkyl, alkoxycarbonyl, aryloxycarbonyl or acyl.

New compounds of the formula $R_d-NX-CO-NX'H$ where X and X' are different and are (1) chloro or bromo and (2) hydrogen and $R_d$ is alkyl or cycloalkyl, 3–15 carbon atoms, or $R_1C(O)-$, where $R_1$ is aliphatic, cycloaliphatic, aryl, alkoxy or aryloxy, each of not more than 10 carbon atoms and when X is H, X' is Cl or Br and $R_d$ is alkyl or cycloalkyl and when X is Cl or Br, X' is H and $R_d$ is $R_1C(O)-$.

6 Claims, No Drawings

N-MONOHALOMONOSUBSTITUTED UREAS

RELATED APPLICATION

This is a continuation division of application Ser. No. 684,651, filed Nov. 21, 1967, now U.S. Pat. No. 3,746,760 which in turn is a continuation-in-part of application Ser. No. 409,306, filed Nov. 5, 1964 (now abandoned).

This invention relates to the preparation of N-monohalomonosubstituted urea; also to the preparation of hydrazine derivatives; also to the preparation of azo compounds. Further, the invention relates to a new class of N-monohalomonosubstitutedureas, including N-monochloro-N-(alkoxycarbonyl) ureas; a new class of hydrazine derivatives; and new classes of azoformates and azocarboxamido compounds.

An object of the invention is a process for the preparation of N-monohalomonosubstituted ureas by direct halogenation of the corresponding monosubstituted ureas.

Another object of the invention is a process of direct halogenation of monosubstituted ureas to N-monohalomonosubstituted ureas, in high yield.

Still another object of the invention is a process for the preparation of hydrazine derivatives, both disubstituted and monosubstituted.

Yet another object of the invention is a process for the preparation of hydrazine derivatives from readily available chemical intermediates.

A particular object of the invention is a process which can be controlled to the substantial preparation only of disubstituted or monosubstituted hydrazine derivatives.

Another particular object of the invention is a process for the preparation of unsymmetrical disubstituted hydrazine derivatives.

Other objects of the invention will become apparent in the course of the detailed description of the invention.

SUMMARY

N-Monohalomonosubstituted Urea Invention

In this process of the invention, a monosubstituted urea, (I) RNH-CO-NH$_2$, is reacted with freehalogen, preferably chlorine. The urea is in the form of a suspension in liquid water. At least about two gram atoms of halogen is added per mole or urea reactant, usually about 100–200% of this proportion depending upon the monosubstituted urea feed. The halogenation is carried out at a temperature of about 0°–60°C. The halogen becomes attached at either the 1 or the 3 position — counting from the R side of the formula — depending upon whether a carbonyl or alkyl carbon is attached to the urea nitrogen area. R is either alkyl having at least 3 carbon atoms, cycloalkyl, aralkyl, acyl, alkoxycarbonyl or aryloxycarbonyl.

A particular urea reactant is an alkoxycarbonyl urea,

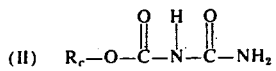

where R$_c$ is either alkyl, cycloalkyl, aryl, aralkyl or heteroalkyl. Here the halogen preferentially attaches to the interior nitrogen to give, for example, an N-chloro-N-(alkoxycarbonyl) urea product.

In some cases, the yield of the defined halourea is improved and the usage of free halogen decreased by having present in the aqueous reaction medium an acceptor for the hydrogen halide by-product of the halogenation reaction. Zinc oxide is a preferred acceptor. The acceptor desirably is present in about the stochiometric requirement.

The new class of N-monohalomonosubstituted ureas of the invention is,

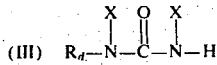

where X and X' are different and are either chlorine, bromine or hydrogen; and R$_d$ is either alkyl, cycloalkyl — each having 3–15 carbon atoms — and R$_1$C(O)— and R$_1$ is aliphatic, cycloaliphatic aryl, alkoxy, or aryloxy, each having not more than 10 carbon atoms; and said radicals having the following relation: (a) when X is hydrogen, X' is chloro or bromo, and R$_d$ is said alkyl or cycloalkyl; and (b) when X is chloro or bromo, X' is hydrogen and R$_d$ is R$_1$C(O)—.

The Hydrazo Invention

In this process of the invention a N-monohalomonosubstituted urea,

is reacted with an alkaline material in the presence of a compound (reactant) affording a reactive hydrogen. It is essential that at no time should there be an excess of N-chloro compound over the alkaline material, in order to get high yields. An organic reaction medium tends to result in the disubstituted hydraziine reaction product; an aqueous reaction medium tends to result in both disubstituted and monosubstituted hydrazine reaction products, depending upon the conditions. The R$_m$ group is either alkyl, having at least 3 carbon atoms, cycloalkyl, aralkyl, alkoxycarbonyl or aryloxy carbonyl. X and X' are different; one being chloro or bromo and the other being hydrogen. The reaction is usually carried out at a temperature of about 0°–100°C.

Commonly the reactant compound is water, ammonia, carboxylic acid (R$_c$COOH), primary alcohol, (R$_c$OH), primary mercaptan (R$_c$SH), primary amine (R$_c$NH$_2$) and secondary amine [(R$_c$)$_2$NH] where R$_c$ is either alkyl, cycloalkyl, aryl or aralkyl, i.e., R$_c$ as in (II) supra. In some cases the reaction medium may also be the reactant affording the reactive hydrogen.

A particular urea reactant is

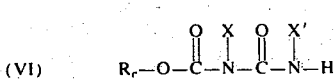

where R$_c$ is as defined in (II) supra; X and X' are as defined in (III) and (V) supra.

The reaction product may be either a mono or disubstituted hydrazo compound, that is, a compound including the hydrazo group

The new class of hydrazo compounds of the invention is, (VII)　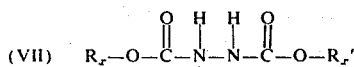

where $R_x$ and $R'_x$ are different and are either alkyl, cycloalkyl, aryl, aralkyl, alkali metal and alkaline earth metal.

The Azo Invention

Azo compounds as used herein are compounds including the azo group, —N=N—. Many procedures are known for the conversion of a hydrazo compound to the corresponding azo compound. Any of these can be applied to the particular hydrazo compounds to produce the new class of azo compounds of the invention.

A new class of azo compounds is, (VIII)　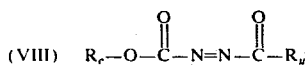

where $R_y$ is either —$OR_z$, $R_z$ or hydrogen; $R_c$ and $R_z$ are different and are either alkyl, cycloalkyl, aryl and aralkyl.

The azodiformates are of particular interest especially when $R_c$ and $R_z$ are alkyl having 1–8 carbon atoms. These are, (IX)　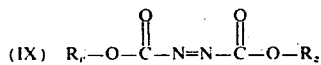

Another new class of azo compounds is directed to the azocarboxamides and the azocarboxamido compounds, i.e., (X)　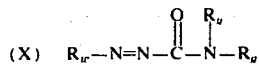

where $R_w$ is

$R_q$ is either $R_c$ or hydrogen; $R_c$ is either alkyl, cycloalkyl, aryl and aralkyl.

DESCRIPTION

N-Monohalomonosubstituted Urea Invention

As is pointed out in the summary, in this process a urea as defined at (I) is reacted with free-halogen, either chlorine or bromine. Chlorine is preferred.

An important feature of this process lies in the use of a liquid reaction medium consisting essentially of water. The define ureas (I) are of low water solubility and the reaction is carried out with the ureas (I) in the form of finely divided particles or droplets suspended in the liquid water. The halogenation reaction proceeds to the desired degree even though the urea reactant is immiscible and the halogenated urea reaction product (V) is also of low water solubility. A minimum amount of water is used as determined by the ability to maintain a uniform suspension of the urea (I). In general about 5–10 volumes of water are used for each volume of urea (I).

The halogenation reaction is carried out at an effective temperature of between about 0° (zero) C and about 60°C. Commonly the reaction temperature is about 5°–25°C.

Sufficient defined free-halogen is introduced into the reaction medium to afford at least about two gram atoms of halogen per mole of defined urea (I) reactant. In order to obtain the desired degree of halogenation, in general, an excess of halogen may have to be introduced. In some instances the stoichiometric amount is sufficient. In general the free halogen is charged in an amount of about 100–200% of the set-forth proportion, i.e., about 2–4 gram atoms of halogen per mole of urea (I).

It has been discovered that, in some cases, the yield of desired reaction product (V) is increased and the use of halogen decreased when there is present in the reaction medium an acceptor for the hydrogen halide byproduct of the reaction. This acceptor may be any compound which does not interfere with the halogenation reaction. It is desirable to use an acceptor which can be readily separated from the defined halogenated urea — preferably the acceptor-hydrogen halide reaction product is water soluble. Especially preferred acceptors, such as zinc oxide, maintain the pH of the aqueous reaction medium on the acid side and afford a water soluble reaction product.

The acceptor is present in about the amount needed to react with the hydrogen halide produced. It is desirable to use only about the necessary amount of acceptor.

When chlorinating the urea (I) using zinc oxide acceptor for the hydrogen chloride by-product, it has been found that the desired monochloro urea product is obtained when the chlorine is charged in an amount of 100–120% of the set-forth proportion.

The monohalo urea product (V) is water insoluble and is easily isolated in high purity by simple filtration, water washing of the filter cake, and then drying of the washed cake.

A limited number of N-monochloromonosubstituted ureas are known. All of these are of the configuration:

(XXI)　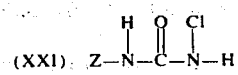

where Z is the "art" substituent, and the chloronitrogen is number 3 in urea naming. The other possible isomer is:

(XII)　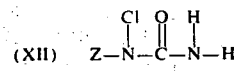

where the chloronitrogen is number 1 in urea naming. None of these are reported in the art.

This process of the invention has permitted the production of new N-monohalomonosubstituted urea having the formula:

(III)　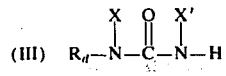

The process of this invention produces monohaloureas in both the isomeric forms as represented by formula V supra. The isomer XI is obtained from alkyl, cycloalkyl, and aralkylurea while the isomer XII is obtained from alkyl, cycloalkyl, and aralkylurea while the isomer XII is obtained from alkoxycarbonyl, aryloxycarbonyl, and acylureas.

In ureas containing a carbonyl group attached to one of the nitrogens, e.g.

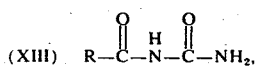

the hydrogen remaining on this carbonyl substituted nitrogen is much more acidic than the two hydrogens attached to the other urea nitrogen atom. This is evidenced by the fact that while ethoxycarbonylurea,

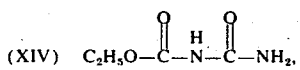

is insoluble in water, it is very soluble in aqueous dilute sodium hydroxide. It is quantitatively precipitated from such an alkaline solution by acidification; thus it forms soluble sodium salts through this acidic hydrogen. Therefore, this highly acidic hydrogen is preferentially displaced by the positive chlorine in making the N-chloro compounds of these carbonyl containing ureas by direct aqueous chlorination. Thus, whereas the prior art indicates that the monosubstituted-N-chloroureas previously known are all of the structure XI above, the present process produces those of structure XII above from ureas containing a carbonyl group attached to one of the nitrogen atoms as evidenced by infrared spectroscopy wherein the Amide II band characteristic of monosubstituted amides is no longer present in these N-chloro derivatives.

EXAMPLES A

The following procedures were used for the Preparation of Monosubstituted N-Chlorourea isomers:

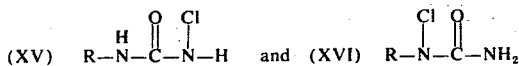

Chlorine gas was admitted into an aqueous stirred suspension containing 0.10 mole of the monosubstituted urea, 0.03 to 0.05 mole of zinc oxide and 50 to 200 ml. of water at 0°–60°C until about 0.10 mole, usually, of chlorine was absorbed. Some compounds needed an excess of chlorine. After stirring for an additional 15 to 60 minutes, the reaction mixture was filtered and the white solid product washed well with water. The resultant monosubstituted N-chloroureas were dried in a vacuum desiccator over calcium chloride to constant weight. Melting points, infrared spectra and active chlorine analysis were determined on the products. All melted with decomposition (dec.).

In preparing liquid N-chloro-N'-alkylureas, chlorine gas was passed into an aqueous stirred suspension containing 0.10 mole of the monosubstituted urea and 50 ml water until 0.10 mole of chlorine was absorbed at 0° to 50°C. After stirring for an additional 5 to 60 minutes, 25 ml $CH_2Cl_2$ was added, the reaction stirred an additional 10 minutes and the $CH_2Cl_2$ layer separated. The $CH_2Cl_2$ layer was washed twice with 20 ml portions of water, dried over anhydrous $Na_2SO_4$, filtered and the $CH_2Cl_2$ stripped off.

Various derivatives were prepared according to these procedures, these are listed in Table A.

TABLE A

| Monosubstituted Urea Feed | % Yield of the N-Chloro Derivative | m.p. of the N-Chloro Derivative, °C | % Purity of the N-Chloro Derivative |
|---|---|---|---|
| N-(methoxycarbonyl)urea | 80.2 | 169–171 dec. | 98.8 |
| N-(ethoxycarbonyl)urea | 92.0 | 149–151 dec. | 99.3 |
| N-(isopropoxycarbonyl)urea | 68.0 | 143–145 dec. | 99.2 |
| N-(t-butoxycarbonyl)urea | 94.7 | 73–86 dec. | 96.9 |
| t-Butylurea | 89.0 | 100–101 dec. | 100.0 |
| Pivaloylurea | 94.6 | 134–136 dec. | 98.0 |
| N-(1-methylcyclohexyl)urea | 66. | — | 100.0 |
| Cyclohexylurea | 95.7 | 111–114 dec. | 99.0 |
| Acetylurea | 81.4 | 160–162 dec. | 99.7 |
| Benzoylurea | 90.0 | 148–150 dec. | 96.9 |
| t-cumylurea | 85 | 104–106 dec. | 100.0 |
| t-amyl urea | 82 | 67–70 | 99% |
| n-butyl urea | 57 | 49–57 | 91% |
| dodecyl urea | 66 | 65–69 | 80% |
| isobutyl urea | 66 | liquid | — |
| isopropyl urea | 46 | liquid | — |
| n-propyl urea | 72 | liquid | — |

The liquid alkyl-N'-chloroureas were isolated by solvent extraction as shown. However, a solvent is not really necessary since these liquid alkyl-N'-chloroureas were not soluble in the water reaction medium. A simple separation of the organic and aqueous layers can be used.

Methylurea and ethylurea dissolved in the water reaction medium and therefore their N'-chloro derivatives could not be made by this process. No products were isolated from these attempted chlorinations.

EXAMPLE A¹

1-chloro-1-(ethoxycarbonyl)urea was prepared without a hydrogen chloride acceptor. A 100% excess of chlorine gas had to be used to obtain a satisfactory purity level of product.

Under the same conditions, except that zinc oxide was present, a satisfactory purity level was obtained at a 10% excess chlorine usage.

EXAMPLE A²

PREPARATION OF 1-CHLORO-3-(1-METHYLCYCLOHEXYL)UREA

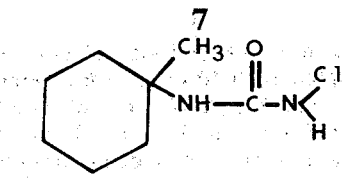

To a rapidly stirred slurry of 7.5 g (.048m) of N-(1-methylcyclohexyl)urea in 75 ml. water at 15°C was added 3.36g. (.048 m) of chlorine at 0.5 g/minute. The reaction mixture was stirred an additional ½ hour at 15°C and filtered. The filter cake was washed with cold water until free of acid and air dried overnight. The white solid weighed 6.0 g (66% yield) and contained 18.9% active chlorine (calculated value for 1-chloro-3-(1-methylcyclohexyl)urea = 18.5% active chlorine).

EXAMPLE A[3]

PREPARATION OF 1-CHLORO-3-(t-CUMYL)UREA

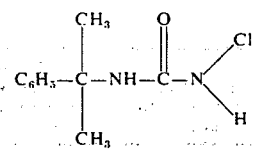

A slurry of 12.0 g (.0675 m) of t-cumylurea in 70 ml water at 35°C was stirred at high speed until the t-cumylurea became finally dispersed (10–15 minutes) and then the temperature was lowered to 15°C. Chlorine was passed into the slurry at 0.2-0.3 g/minute until 4.5 g chlorine had been absorbed. The reaction was stirred on additional ½ hour at 10°C, filtered, washed with water until free of acid and dried. The white solid weighed 12.2 g (85% yield) and had a m.p. of 100°–105°C. After washing with pentane, the 1-chloro-3-t-cumylurea melted at 104°–106°C and contained 16.97% active chlorine (calculated value = 16.7% active chlorine).

The Hydrazo Invention

In the hydrazo process a hydrazine derivative is prepared by the controlled reaction of a N-monohalomonosubstituted urea, (V) $R_m$—NX—CO—NHX', with an alkaline material in the presence of a compound (reactant) affording an active hydrogen. Chlorine is the preferred halogen. An essential feature of this process is that the alkaline material is present throughout the reaction time in an amount at least equal to the N-halourea.

An organic liquid which may or may not be a solvent for the halourea reactant (V) may be used as a reaction medium. The halourea reactant (V) may be suspended in an organic liquid or in a water reaction medium. It has been observed that the use of an organic liquid reaction medium tends to result in a disubstituted hydrazine product. The monosubstituted hydrazine product can be obtained as the exclusive product by using a water reaction medium.

The organic liquid and the water medium may also function as the reactant affording an active hydrogen – this is the preferred operation.

Preferably the reaction is carried out by adding the halourea, the active hydrogen reactant and the alkaline material incrementally and essentially simultaneously into the reaction zone in amounts to afford an excess of alkaline material in the reaction zone throughout the reaction time. Incremental includes a continuous flow at a controlled rate. Alternatively, the halourea is added to the alkaline solution of the active hydrogen reactant.

In general the hydrazo reaction is carried out at a temperature of 0°–100°C. The reaction can be carried out in two stages of temperature: (1) about 10°–30°C; (2) about 60°–100°C. Although a fair yield of hydrazine product is obtained at the lower temperatures, the second stage ensures complete reaction. In many cases the second stage is not necessary.

The preferred active hydrogen reactants are water, ammonia, carboxylic acids, $R_cCOOH$; primary alcohols, $R_cOH$; primary mercaptans, $R_cSH$; primary amines, $R_cNH_2$ and secondary amines, $(R_c)_2NH$.

The alkaline material is desirably an alkali metal hydroxide or an alkaline earth metal hydroxide, or the corresponding alkoxides. Other alkaline materials that are capable of extracting a proton from one of the nitrogens of the defined N-halourea can also be used.

In the process the molar ratio of halourea reactant to alkaline material is not permitted to exceed 1.0 in the reaction zone. This mode of operation affords high yields and high purity hydrazine products. It is postulated that an intermediate isocyanate compound, R—NHN=C=O, is produced. If the halourea reactant should be present as such, it is believed a reaction takes place with the postulated isocyanate to form undesired side reaction products thereby decreasing yield and purity of the desired hydrazo product.

The hydrazo process of the invention has enabled the production of a new class of hydrazine compounds, as well as species not previously prepared of known classes of hydrazine compounds. This new class of hydrazo compounds has the formula:

(VII) 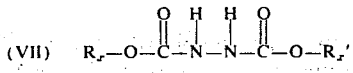

where $R_r$ and $R'_r$ are different and are either alky, cycloalkyl, aryl, aralkyl, alkali metal and alkaline earth metal. Broadly this class of compounds (VII) are unsymmetrical hydrazodiformates, e.g., methyl ethyl hydrazodiformate; methyl t-butylhydrazodiformate; isopropyl ethyl hydrazodiformate; sodium ethyl hydrazodiformate; and methyl isopropyl hydrazodiformate.

EXAMPLE B

Mono- and 1,2-disubstituted hydrazo compounds were prepared by Procedure B below. The monosubstituted hydrazines were also prepared by Procedure B[1] below. Procedure B is preferred for preparing the 1,2-disubstituted hydrazines and Procedure B[1] for preparing the monosubstituted hydrazines.

Procedure B: Into one dropping funnel was placed 0.05 to 0.20 moles of a base dissolved in 50 to 100 ml. of the solvent. Into another dropping funnel was placed a solution, or a suspension, as the case may be, of 0.045 to 0.10 mole of a monosubstituted N-chlorourea in 50 to 100 ml of the active hydrogen solvent. A stirrer was usually employed in the second funnel and a drying tube was attached to the top of the first dropping funnel when anhydrous bases were used.

Materials from the two funnels were simultaneously added to a rotating Vigreux column draining into a receiver flask cooled in an ice bath. The rates of addition were such that the mole ratio of the N-chlorourea to the base in the column never exceeded 1.0. The temperature of the rotating column was usually between 20° and 30°C, although lower and higher temperatures can be used. The addition times were usually 6 to 10 minutes. In batch processes, the funnels and the column were usually washed with some of the solvent.

To prevent ester interchange when methyl ethyl hydrazo esters were being prepared in methanol or ethanol solvent, the excess base was neutralized with hydrogen chloride, below room temperature, after the additions were completed.

The cool flask, containing the reaction mixture, was then immersed into a hot oil bath and a reflux condenser attached. After refluxing for 30 minutes, the reaction mixture was cooled again in an ice water bath where any excess base, if not neutralized previously, was neutralized with hydrogen chloride.

The disubstituted hydrazine compounds were then isolated in admixture with sodium chloride by distilling off the organic solvent. The infrared spectra of the hydrazine compounds thus obtained indicated that they were of sufficient purity for oxidation to the corresponding azo compounds. Sodium chloride is transparent in the infrared and its presence is beneficial in the oxidation step.

Samples of the pure disubstituted hydrazine compounds were obtained by washing out the sodium chloride with water, when the hydrazine compound possessed only limited or no solubility in water. The water soluble hydrazine compounds were isolated either by extracting them out of a sodium chloride saturated water solution with a suitable organic solvent, or by taking them directly into an organic solvent in which sodium chloride is insoluble. Recrystallization of the hydrazine compounds isolated by these techniques was usually not required, although very pure samples were readily prepared by recrystallization.

Procedure B[1]: To a rapidly stirred solution of sodium hydroxide in watter (8–16%) at 10°–25°C, was added the pure monosubstituted-N-chlorourea in ⅛ to 1/5 the molar amount of sodium hydroxide present over a 1 to 1 ½ hour time interval. After the addition was completed, the reaction mixture was stirred for an additional 15 to 60 minutes and then filtered to remove the small quantities of by-products usually formed. The filtrate was then acidified with a mineral acid (e.g., sulfuric acid or hydrochloric acid) to a pH of about 2. to obtain an aqueous solution of the mineral acid salt of the monosubstituted hydrazine, the concentration of which was determined by an iodometric titration. The pure salt was isolated by evaporating the aqueous solution to dryness and dissolving the hydrazine salt in alcohol, filtering, and evaporating the alcohol. In some cases, the hydrazine salt was crystallized from the aqueous reaction mixture by concentrating and cooling. The free monosubstituted hydrazines can also be obtained by extracting the sodium chloride saturated aqueous reaction solution with a water immiscible organic solvent for the hydrazine compound and then evaporating off the solvent.

Comments about the free acid 17 and sodium salt 18 in Table B: — When the reaction is carried out with one mole of sodium hydroxide per mole of 1-chloro-1-(ethoxycarbonyl)urea, the free acid is formed. With 2 moles of sodium hydroxide, the sodium salt is formed. Actually 2 moles of sodium hydroxide were used in both cases. The free acid was produced by careful neutralization of the sodium salt. In neither case were the pure products isolated since decarboxylation to ethyl carbazate is a side reaction at low temperatures and the only reaction at higher temperatures. Infrared and chemical evidence proved the existence of both the free acid and the sodium salt in the reaction mixture. The yields of both compounds, however, were low.

The data on these reactions and the products are given in Table B.

TABLE B

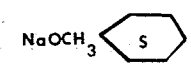

| R | Act. H Cpd | BASE | Product | % YIELD | M.P., °C. |
|---|---|---|---|---|---|
| 1. $(CH_3)_3C-$ | $CH_3OH$ | $NaOCH_3$ | $(CH_3)_3C-N(H)-N(H)-C(=O)-OCH_3$ | 93.7 | 70 |
| 2. Cyclohexyl | $CH_3OH$ | $NaOCH_3$ ⟨S⟩ | $-N(H)-N(H)-C(=O)-OCH_3$ | 57.3 | 54–57 |
| 3. $CH_3O-C(=O)-$ | $C_2H_5OH$ | $NaOC_2H_5$ | $CH_3O-C(=O)-N(H)-N(H)-C(=O)-OC_2H_5$ | 72.5 | Liquid |
| 4. $CH_3O-C(=O)-$ | $C_2H_5OH$ | $NaOC_2H_5$ | $C_2H_5O-C(=O)-N(H)-N(H)-C(=O)-OC_2H_5$ | 71.6 | 127 |
| 5. $C_2H_5O-C(=O)-$ | $CH_3OH$ | $NaOCH_3$ | $CH_3-O-C(=O)-N(H)-N(H)-C(=O)-OCH_3$ | 89 | |
| 6. $C_2H_5O-C(=O)-$ | $C_2H_5OH$ | $NaOC_2H_5$ | $C_2H_5O-C(=O)-N(H)-N(H)-C(=O)-OC_2H_5$ | 86.5 | 129–131 |

TABLE B-continued $$R-\underset{\underset{Cl}{|}}{N}-\underset{\underset{O}{\|}}{C}-N\diagup_H^H \text{ and/or } R-\underset{\underset{H}{|}}{N}-\underset{\underset{O}{\|}}{C}-N\diagup_H^{Cl} + \underset{Cpd}{Act.H} \xrightarrow{BASE} -\underset{\underset{H}{|}}{N}-\underset{\underset{H}{|}}{N}-\text{product}$$

| R | Act. H Cpd | BASE | Product | % YIELD | M.P., °C |
|---|---|---|---|---|---|
| 7. (CH₃)₂CHO—CO— | C₂H₅OH | NaOC₂H₅ | (CH₃)₂CHO—CO—NH—NH—CO—OC₂H₅ | 80.8 | 62–65 |
| 8. (CH₃)₃C—O—CO— | CH₃OH | NaOCH₃ | (CH₃)₃C—O—CO—NH—NH—CO—OCH₃ | 70.0 | 99–101 |
| 9. C₂H₅O—CO— | H₂O | NaOH | C₂H₅O—CO—NHNH₂·HCl | 23.6 | 124–127 |
| 12. (CH₃)₃C— | NH₃ | NaNH₂ | (CH₃)₃C—NH—NH—CO—NH—H | — | 180.5–182.0 |
| 13. C₂H₅O—CO— | NH₃ | NH₄OH | C₂H₅O—CO—NH—NH—CO—NH₂ | 44.4 | 105–110 |
| 14. (CH₃)₂CHO—CO— | CH₃OH | NaOCH₃ | (CH₃)₂CHO—CO—NH—NH—CO—OCH₃ | 89.0 | 88–90 |
| 15. C₂H₅O—CO— | n-C₄H₉NH₂ | n-C₄H₉NH₂OH | C₂H₅O—CO—NH—NH—CO—NH—C₄H₉-n | — | 100–105 |
| 16. C₂H₅O—CO— | H₂O | NaOH | C₂H₅O—CO—NH—NH—CO—OH | — | — |
| 17. C₂H₅O—CO— | H₂O | NaOH | C₂H₅—O—CO—NH—NH—CO—ONa | — | — |
| 18. CH₃O—CO— | CH₃OH | NaOCH₃ | CH₃O—CO—NH—NH—CO—OCH₃ | 81.7 | 120–122 |
| 19. (CH₃)₃C— | H₂O | NaOH | (CH₃)₃CNHNH₂·HCl | 92 | 194–197 |
| 20. t-C₅H₁₁— | H₂O | NaOH | t-C₅H₁₁NHNH₂·HCl | 76 | 122–127 |
| 21. 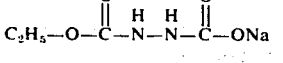 | H₂O | NaOH | 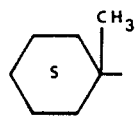 | 52 | — |
| 22. C₆H₅—C(CH₃)₂— | H₂O | NaOH | C₆H₅—C(CH₃)₂—NHNH₂·H₂SO₄ | 78.3 | 200–205 |

(Compounds 19–22 were made by Procedure B¹.
All others in Table B were made by Procedure B).

EXAMPLE B²

PREPARATION OF t-BUTYLHYDRAZINE HYDROCHLORIDE

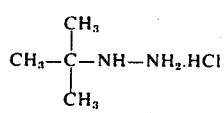

To a rapidly stirred solution of 16.4g (.41m) of sodium hydroxide in 150 ml water in a 250 ml. 4 neck round bottom flask was added 20.6g (.127m) of 93% N chloro-N'-t-butylurea over 1 hour holding the temperature at 5°C±2° with an ice bath. The reaction was stirred an additional ½ hour at 5°C and filtered. The insolubles were discarded and the filtrate was acidified to pH 2 by the slow addition of conc. HCl (CO₂ is evolved). The acidified filtrate weighed 221.5g and assayed 6.56% t-butylhydrazine hydrochloride. The yield of t-butylhydrazine hydrochloride was 14.5 (92%).

The aqueous solution was evaporated to dryness and the t-butyl-hydrazine hydrochloride extracted from the sodium chloride with warm ethanol. The ethanol solution was filtered and the ethanol concentrated and cooled to 5°C. The t-butylhydrazine crystallized out of solution. The t-butylhydrazine hydrochloride was filtered and washed with cold ethanol and dried in the hood overnight. The dried material had a m.p. of 194°–197°C and assayed 99 ½% as t-butylhydrazine hydrochloride by iodometric titration.

EXAMPLE B³

PREPARATION OF t-AMYLHYDRAZINE HYDROCHLORIDE

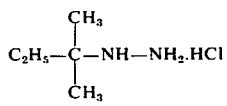

To a rapidly stirred solution of 38.8 g (.966 m) of sodium hydroxide in 300 ml water in a 500 ml 4 neck round bottom flask was added 53g (0.32 m) of 96% N-chloro-N'-t-amylurea over 1 hour holding the temperature at 20°C±2° with a cold water bath. The reaction was stirred an additional two hours at 25°C and filtered. The insolubles were discarded and the filtrate was acidified to pH 2 by the slow addition of 95 ml conc. HCl($CO_2$ is evolved). The acidified filtrate weighed 513g and assayed 6.6% t-amyl-hydrazine hydrochloride. The yield of t-amylhydrazine hydrochloride was 33.8g (76%).

The aqueous solution was evaporated to dryness and the t-amylhydrazine hydrochloride extracted from the sodium chloride with ethanol. The ethanol solution was filtered and the ethanol evaporated to dryness leaving a white solid with a m.p. of 122°–127°C, which assayed 86% as t-amylhydrazine hydrochloride by iodometric titration.

EXAMPLE B⁴

PREPARATION OF 1-(METHYLCYCLOHEXYL)HYDRAZINE SULFATE

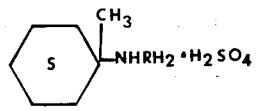

To a rapidly stirred solution of 5.1 g (.128m) of sodium hydroxide in 50 ml water was added 6.0g (.0317m) of 1-chloro-3-(1-methylcyclohexyl)urea in small increments over 1 hour holding the temperature at 15°C with a cold water bath. The reaction mixture was stirred an additional ½ hour at 15°C and filtered. The filtrate was acidified to a pH of 2 with 77% $H_2SO$. The aqueous solution weighed 66.3g and assayed 5.6% as 1-(methylcyclohexyl)-hydrazine sulfate (52% yield) by iodometric titration.

EXAMPLE B⁵

PREPARATION OF t-CUMYLHYDRAZINE SULFATE

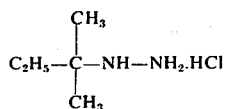

To a rapidly stirred solution of 9.3 g (.235m) of sodium hydroxide in 95 ml water cooled to 15°C in a water bath was added 12.9 g (.058m) of 96% 1-chloro-3-t-cumylurea in small increments over 1¼ hour holding the temperature at 15°C±2°. After the addition was over, the cold water bath was removed and the reaction stirred 1¼ hour, the temperature rising to room temperature. The reaction mixture was acidified with 77% $H_2SO_4$ to pH 1. A small amount of insoluble material formed on the surface and this was filtered off. The aqueous solution weighed 142 g and assayed 7.92% t-cumylhydrazine sulfate (78.3% yield) by iodometric titration.

The t-cumylhydrazine sulfate solution was concentrated until some solid began to come out of solution. The solution was cooled in the refrigerator for 1/2 hour and the crystallized solids filtered off. The solid t-cumylhydrazine sulfate had a m.p. of 200°–205°C.

The Azo Invention

Any of the hydrazo compounds may be converted to the corresponding azo compounds by one or other of the procedures known for this conversion.

Previously known azo compounds can be prepared much more readily from intermediates produced by the halourea and hydrazo process; many species not previously known have been prepared. Also, two new classes of azo compounds have been discovered. These new classes have the formulas:

(VIII) 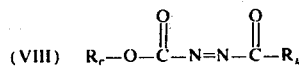

(X) 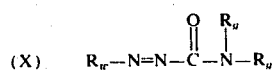

where $R_w$ is

$R_g$ is either $R_c$ or hydrogen; $R_y$ is either $-OR_z$, $R_z$ or hydrogen and $R_c$ and $R_z$ are different and are either alkyl, cycloalkyl, aryl, aralkyl and heteroalkyl.

The azodiformate sub-class of VIII is of particular interest.

(IX) 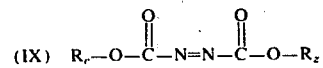

where $R_c$ and $R_z$ are different and are either alkyl cycloalkyl, aryl, aralkyl and heteroalkyl. $R_c$ and $R_z$ as alkyl having 1-8 carbon atoms are of especial interest.

Typical members of these classes are methyl ethyl azodiformate; methyl t-butyl azodiformate; methyl pivaloylazoformate; methyl acetylazoformate; ethyl benzoylazoformate; methyl benzoylazoformate and methyl isopropyl azodiformate.

Formulas VIII and X can be consolidated into a single formula, defined as follows:

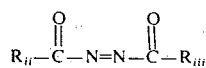

where:
1. $R_{ii}$ is $R_cO-$, $R_zO-$, or Rg;
2. $R_{iii}$ is $R_cO-$, $R_zO-$, or Rg;
3. $R_{ii}$ and $R_{iii}$ are different;
4. Also $R_{iii}$ may be

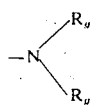

and when $R_{iii}$ is the aforesaid amide then $R_{ii}$ is Rg;
5. Rg is $R_c$ or Hydrogen; and
6. $R_c$ and $R_z$ are different and are each alkyl, cycloalkyl, aryl or aralkyl radicals.

EXAMPLES C

In the dehydrogenation of the hydrazo compounds to the corresponding azo compounds, chlorine gas was passed into a stirred reaction mixture containing 50 ml. of water, 50 ml. of methylene chloride and 2 to 5 grams of the hydrazo compound at 0°–20°C. until 0% to 10% excess of the calculated required amount of chlorine was absorbed. After the chlorine additions were completed, the reaction mixtures were stirred for an additional 30 minutes at 0°–15°C. The aqueous layers were separated, extracted once with methylene chloride and discarded. The combined methylene chloride layers were washed with water and then with 10% sodium bicarbonate until no further bleaching of pH paper was observed in the washings. After further washing with water, the methylene chloride solutions were dried over anhydrous sodium sulfate, filtered, and the methylene chloride distilled to leave the azo compounds in relatively high purity. Infrared spectra and hydrogen iodide titrations (showing the oxidizing ability of these azo compounds) were used to determine purity. Typical results are given in Table C.

TABLE C

| $R_i-\overset{H}{N}-\overset{H}{N}-\overset{O}{\overset{\|}{C}}-R_{ii} \xrightarrow{-2H} R_i-N=N-\overset{O}{\overset{\|}{C}}-R_{ii}$ | | | |
|---|---|---|---|
| $R_i$ | $R_{ii}$ | % YIELD | PURITY, % |
| a. $CH_3O-\overset{O}{\overset{\|}{C}}-$ | $C_2H_5O-$ | 76.7 | 100.0 |
| b. $(CH_3)_2CHO-\overset{O}{\overset{\|}{C}}-$ | $C_2H_5O-$ | 74.0 | 100.0 |
| c. $(CH_3)_3C-O-\overset{O}{\overset{\|}{C}}-$ | $CH_3O-$ | 96.6 | 100.0 |
| d. $(CH_3)_3C-\overset{O}{\overset{\|}{C}}-$ | $C_2H_5O$ | 90.0 | 97.0 |
| e. $CH_3-\overset{O}{\overset{\|}{C}}$ | $C_2H_5O$ | 65.0 | 72.9 |
| f. $C_6H_5\overset{O}{\overset{\|}{C}}-$ | $C_2H_5O-$ | 90.0 | 98.9 |

TABLE C-continued

| $R_i-\overset{H}{N}-\overset{H}{N}-\overset{O}{\overset{\|}{C}}-R_{ii} \xrightarrow{-2H} R_i-N=N-\overset{O}{\overset{\|}{C}}-R_{ii}$ | | | |
|---|---|---|---|
| $R_i$ | $R_{ii}$ | % YIELD | PURITY, % |
| g. $(CH_3)_2CHO-\overset{O}{\overset{\|}{C}}-$ | $CH_3O-$ | 89.0 | 100.0 |
| h. $C_6H_5-\overset{O}{\overset{\|}{C}}-$ | $n-C_4H_9\overset{H}{N}-$ | 92 | 90.4 |
| i. $(CH_3)_3C-\overset{O}{\overset{\|}{C}}-$ | $n-C_4H_9-\overset{CH_3}{\underset{\|}{N}}-$ | 87.8 | 76.7 |

Besides being intermediates for synthesizing the hydrazo compounds of this invention, the monosubstituted N-chloroureas are also useful as oxidizing agents, chlorinating agents, and disinfectants.

Because of their polyfunctional nature, substituted hydrazines find applications in many places. For example, these materials are useful for producing resins, coatings, adhesives, plastics, insecticides, fungicides, textile treating agents, plasticizers, rubber softeners, blowing agents, and missile and jet fuels.

Uses of azo compounds of the invention include dyes, polymerization catalysts, blowing agents as shown in U.S. Pat. No. 3,306,862, oxidizing agents, and free radical generators.

Oxadiazolin-5-one

When an N-monohalomonoacylurea

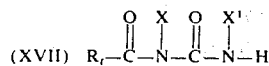

where $R_t$ is alkyl, cycloalkyl, aryl or aralkyl, is reacted with an alkaline material under the conditions of the aforedescribed hydrazo invention, the product has the cyclic structure

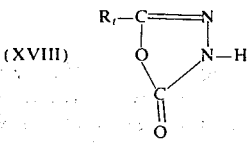

of a 2-substituted - Δ - 1,3,4-oxadiazolin-5-one. These cyclic compounds are reacted with active hydrogen compounds, at temperatures generally higher and longer times of the aforedescribed hydrazo invention, to obtain hydrazine compounds.

Compounds XVIII where $R_t$ is t-butyl, methyl, or phenyl have been prepared.

Throughout this specification the radicals are used in the following sense:
1. Aliphatic and cycloaliphatic are used in the broadest technical sense; it is to be understood that substituents which can be expected to interfere with the reaction are excluded. These radicals which contain only carbon and hydrogen atoms are preferred; as are the mono and di-ring cyclics.
2. Any alkyl having at least 3 carbon atoms or cycloalkyl radical may be used in the process inventions to prepare the various described compounds. Preferably the alkyl or cycloalkyl radicals have a total of 3–15 carbon atoms.

3. Aryl and aralkyl are used in the broadest sense; however, the phenyl and phenalkyl radicals such as benzyl and t-cumyl are preferred.

4. Acyl refers to the

also written RC(O)—, radical where R can be aliphatic, cycloaliphatic, aryl, or aralkyl and the corresponding alkoxy and aryloxy radicals. Preferably R has not more than 10 carbon atoms.

5. Alkoxy, (Alk)—O—, and aryloxy, (aryl)—O—, alkoxy carbonyl,

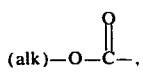

and aryloxycarbonyl,

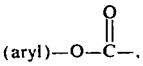

may be derived from any aliphatic or aromatic hydrocarbon radical. It is preferred that alk be alkyl and aryl be phenyl, and have not more than 10 carbon atoms.

Thus, having described the invention, what is claimed is:

1. N-monohalomonosubstituted urea of the formula

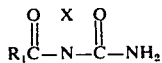

where: X is chlorine or bromine; and $R_1$ is alkoxy or aryloxy of up to 10 carbon atoms.

2. A compound of claim 1 wherein X is chlorine.
3. 1-chloro-1-(methoxycarbonyl)urea.
4. 1-chloro-1-(ethoxycarbonyl)urea.
5. 1-chloro-1-(t-butoxycarbonyl)urea.
6. 1-chloro-1-(isopropoxycarbonyl)urea.

* * * * *